United States Patent [19]
Freedman et al.

[11] Patent Number: 6,147,489
[45] Date of Patent: Nov. 14, 2000

[54] METHOD AND APPARATUS FOR MEASURING TOTAL NUCLEAR MAGNETIC RESONANCE POROSITY

[75] Inventors: Robert Freedman, Houston; Christopher Morriss, The Woodlands, both of Tex.; Austin Boyd, Halifax, Canada; Charles Flaum, Ridgefield, Conn.

[73] Assignee: Schlumberger Technology Corporation, Houston, Tex.

[21] Appl. No.: 08/873,981

[22] Filed: Jun. 12, 1997

Related U.S. Application Data

[60] Provisional application No. 60/042,059, Apr. 9, 1997.

[51] Int. Cl.$^7$ .................................................... G01V 3/00
[52] U.S. Cl. ................................................................ 324/303
[58] Field of Search ............................................. 324/303

[56] References Cited

U.S. PATENT DOCUMENTS

| | | | |
|---|---|---|---|
| 5,023,551 | 6/1991 | Kleinberg et al. | 324/303 |
| 5,055,787 | 10/1991 | Kleinberg et al. | 324/303 |
| 5,291,137 | 3/1994 | Freedman . | |
| 5,486,762 | 1/1996 | Freedman et al. . | |
| 5,498,960 | 3/1996 | Vinegar et al. . | |
| 5,557,200 | 9/1996 | Coates | 324/303 |
| 6,032,101 | 2/2000 | Freedman et al. | 702/8 |

FOREIGN PATENT DOCUMENTS

WO 97/01110  1/1997  WIPO .

OTHER PUBLICATIONS

Freedman, et al., "Processing of Data From an NMR Logging Tool", Oct. 1995, SPE 30560, Dallas, TX.

Clavier, et al., "The Theoretical and Experimental Bases for the "Dual Water" Model for the Interpretation of Shaly Sands", 1977, Society of Petr. Eng. Trans. 6859.

Hill, et al., "Bound Water in Shaly Sands—Its Relation to $Q_v$ and Other Formation Properties", 20 Log Analyst 3–19.

*Primary Examiner*—Christine K. Oda
*Assistant Examiner*—Tiffany A. Fetzner
*Attorney, Agent, or Firm*—John J. Ryberg; Brigitte L. Jeffery

[57] ABSTRACT

A method and apparatus for determining gas corrected porosity using nuclear magnetic resonance (NMR) and density measurements is disclosed. The total porosity (TCMR) or an earth formation is determined using an NMR tool. A log output is generated that indicates the density of the formation. The density porosity of the formation is determined from the log output. The difference between the TCMR-density porosity log accurately indicates the presence of gas. A gas corrected porosity, $\phi$, and gas saturation, $S_g$, are determined based upon the density porosity and TCMR.

8 Claims, 7 Drawing Sheets

METHOD AND APPARATUS FOR MEASURING TOTAL NUCLEAR MAGNETIC RESONANCE POROSITY

CROSS-REFERENCES

This present application claims the benefit of U.S. Provisional Application No. 60/042,059 filed Apr. 9, 1997.

BACKGROUND OF THE INVENTION

The present invention relates generally to a method for determining the porosity of an earth formation traversed by a borehole, and more particularly, to a method for measuring the total porosity of an earth formation.

Nuclear magnetic logging tools, such as disclosed in U.S. Pat. No. 4,933,638 issued to Kenyon et al., U.S. Pat. Nos. 5,055,787 and 5,055,788 issued to Kleinberg et al, measure the number and nuclear magnetic resonance (NMR) relaxation rates of hydrogen atoms in the pore space of rocks by measuring the amplitude and decay rate of signals resulting from pulse-echo sequences. The nuclear magnetic logging tools send a stream of RF-pulses into the formation and monitor the returning pulses which are called spin echoes. The signal measured by a nuclear magnetic logging tool, such as the CMR, mark of Schlumberger (Combined Magnetic Resonance) tool, formerly the PNMT, mark of Schlumberger (Pulsed Nuclear Magnetism Tool) is proportional to the mean density of hydrogen nuclei in the fluid that occupies the pore space. Since the hydrogen density in water and liquid hydrocarbons are approximately constant, the detected signal can be calibrated to give the volume fraction of the fluid occupying the pore space.

It has been shown that bound and unbound fluids can be distinguished by their relaxation times in water saturated rock samples. See C. Straley, C. E. Morriss, W. E. Kenyon, and J. J. Howard, *NMR in Partially Saturated Rocks: Laboratory Insights on Free Fluid Index and Comparison with Borehole Logs,* LOG ANALYST, January/February 1995, at 40 (paper presented at the 32nd Annual Logging Symposium, SWPLA, Jun. 16–19, 1991). Water that is bound to clay minerals, water in pores that are too small to be flushed by a feasible pressure gradient, and heavy (viscous) hydrocarbons all relax rapidly. Fluids that relax slowly have low viscosity and reside in large pores. Hence, the slowly relaxing fluids can be extracted from the formation, provided there is sufficient permeability.

The cutoff relaxation time, $T_c$, distinguishing bound fluids from unbound fluids is empirically determined to be 50 msec for spin-lattice relaxation, $T_1$, and 33 msec for spin-spin relaxation, $T_2$, for water saturated sandstones and for 100 psi capillary pressure. With a $T_2$ sensitivity limit of approximately 3 msec, in the presence of clays, silts, or microporosity, heretofore known NMR measurement techniques using the CMR tool may underestimate total rock porosity. Hydrogen nuclei in the rock matrix and some of the clay-bound water relax too rapidly and are not detected by the CMR tool. Thus, the CMR porosity measurement produces an effective porosity that does not include contributions from clay-bound water. See U.S. Pat. No. 5,291,137 issued to Robert Freedman; also see R. Freedman and C. E. Morriss, *Processing of Data From an NMR Logging Tool,* SPE 30560 (paper presented at the SPE Annual Technical Conference and Exhibition, Oct. 22–25, 1995). A need exists, therefore, for a total porosity measurement which is sensitive to fast relaxation times that can be associated with clay-bound water and includes, in addition to free fluid and capillary-bound porosity, the porosity of clay-bound water and microporosity.

SUMMARY OF THE INVENTION

The above disadvantages of the prior art are overcome by means of the subject invention for an apparatus and method for indicating an attribute of an earth formation traversed by a borehole. An oscillating magnetic field is produced within the borehole in order to induce a plurality of spin echo signals from selected nuclei of the formation. The spin echo signals are measured and a value is determined for each signal. The plurality of signal values are separated into a first set and a second set wherein the first set comprises the early-time echo signals and the second set comprises the remaining echo signals. The second set of echoes are sub-divided into a plurality of groups and a window sum value is generated for each group of the second set, thereby producing a plurality of window sums. An attribute of the formation is determined based upon the plurality of window sums and the value of each signal of the first set.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENT

Figure 1:
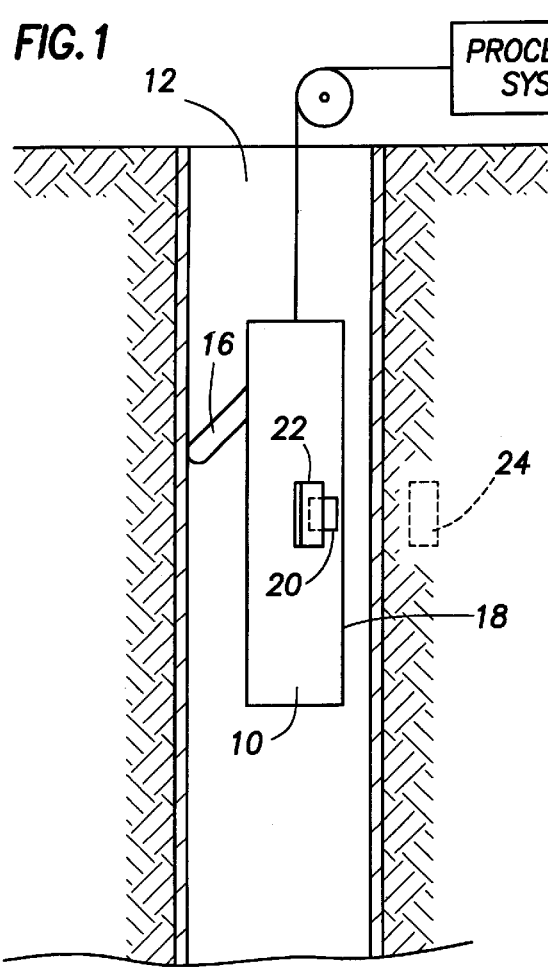
FIG. 1 illustrates a nuclear magnetic resonance logging system.

Referring to FIG. 1, a nuclear magnetic resonance (NMR) logging system is illustrated, the NMR logging system including a NMR logging tool 10 disposed in a borehole 12 and connected via a wireline to a processing system 14 disposed at the borehole surface for processing signals transmitted uphole by the logging tool 10. Alternatively, the processing system 14 may be located downhole. The tool 10 has a retractable arm 16 which, when activated, presses the face 18 against the borehole wall. An antenna 20 and magnet 22 are positioned within the tool 10. The antenna 20 produces an oscillating radio frequency magnetic field and the magnet 22 produces a static magnetic field. The RF magnetic field and the static magnetic field are directed toward a volume of investigation 24 disposed within a portion of the formation traversed by the borehole 12. In operation, the tool 10 makes a measurement in the volume of investigation 24 by magnetically reorienting the nuclear spins of particles in the formation with a pulse of the oscillating magnetic field, and then, detecting the precession of the tipped particles in the static, homogeneous field within the volume of investigation 24 over a period of time.

Figure 2:
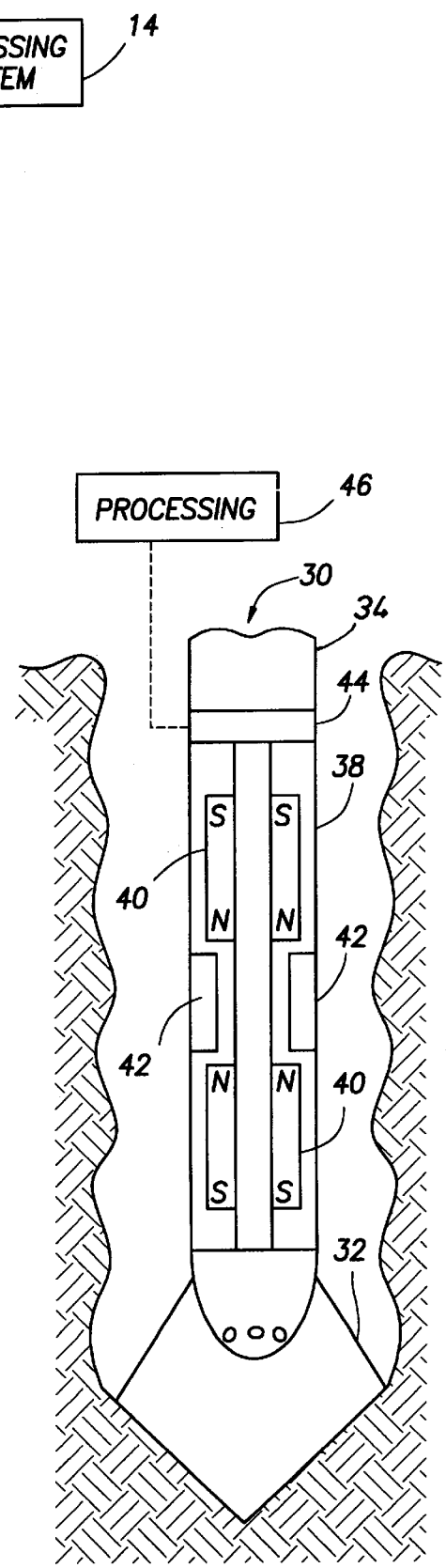
FIG. 2 illustrates a logging-while-drilling nuclear magnetic resonance logging system.

The present invention is useful in a logging-while-drilling application. FIG. 2 illustrates an NMR logging-while-drilling tool. The tool 30 includes a drill bit 32, drill-string 34, and a pulsed NMR device housed within the drill collar 38. The pulsed NMR device comprises a magnet 40, an RF antenna 42, and electronic circuitry 44. The drill collar 38 is the external member that is in contact with the drilling fluid and rock cuttings in the borehole and the earth formation in which the well is drilled. The drill bit 32 and drill string 34 comprise a means for drilling a borehole 12 in the formation. The tool 30 also comprises a means for making pulsed nuclear magnetic resonance (NMR) measurements while a borehole is being drilled. The electronic circuitry 44 comprises a processing system 46 for processing the NMR measurements. Alternatively, the processing system 46 may be located uphole.

Figure 3:
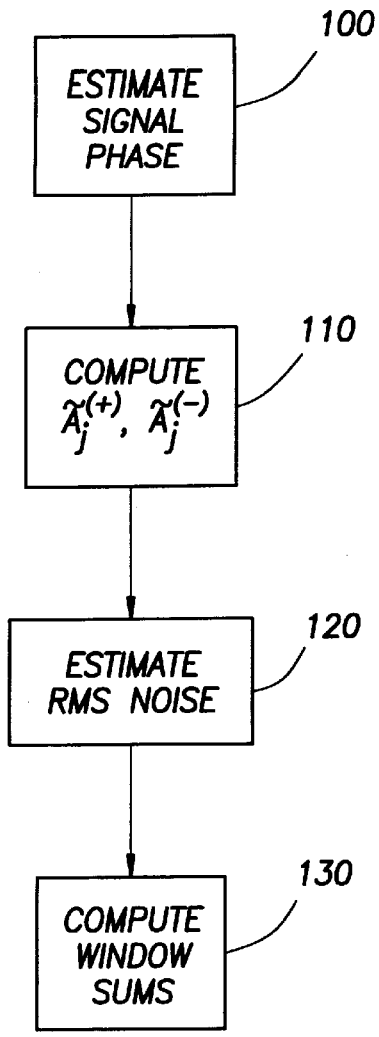
FIG. 3 is a flow chart illustrating a prior art method for determining the effective porosity of a formation.

FIG. 3 illustrates a prior art method for determining effective porosity (CMRP), that is, the sum of free fluid and capillary-bound porosity, using an NMR logging tool. After the NMR logging tool begins energizing the formation with a plurality of RF pulses, the tool begins to receive a plurality of spin-echo pulses from the formation. At step 100, the signal phase, $\theta$, is estimated as a function of the inphase ($R_j$) and quadrature ($X_j$) amplitudes as follows:

$$\hat{\theta} = \arctan\left[\frac{\sum_{j=1}^{J} \tilde{X}_j}{\sum_{j=1}^{J} \tilde{R}_j}\right]. \tag{1}$$

At step 110, the signal plus noise amplitude, ($A_j^{(+)}$), and the amplitude, ($A_j^{(-)}$), for each spin-echo receiver voltage pulse is determined according to the following equation:

$$\tilde{A}_j^{(+)} = \tilde{R}_j\cos\hat{\theta} + \tilde{X}_j\sin\hat{\theta},$$
$$\tilde{A}_j^{(-)} = \tilde{R}_j\cos\hat{\theta} - \tilde{X}_j\sin\hat{\theta}, \tag{2}$$

At step 120, the RMS noise is estimated from the amplitude ($A_j^{(-)}$). Next, at step 130, the window sum $I_{m,m+1}$, is computed from the signal plus noise amplitude ($A_j^{(+)}$). A first window sum, $I_{1,2}$, is determined by summing a plurality of individual signal plus noise amplitudes $A_1^{(+)}, A_2^{(+)}, \ldots, A_n^{(+)}$ which are disposed in a first time window. A second window sum, $I_{2,3}$, is determined in association with a second time window and a third window sum, $I_{3,4}$, is determined in association with a third time window in the same manner as indicated above by summing the associated signal plus noise amplitudes $A_j^{(+)}$ which are disposed within the second and third time windows, respectively. The window sums are transmitted uphole from the NMR tool to a processing system disposed at the surface. The processing system computes a $T_2$ distribution and integrates the distribution function $P(T_2)$ to determine the effective porosity, that is, the sum of free fluid and capillary-bound porosity.

Figure 4:
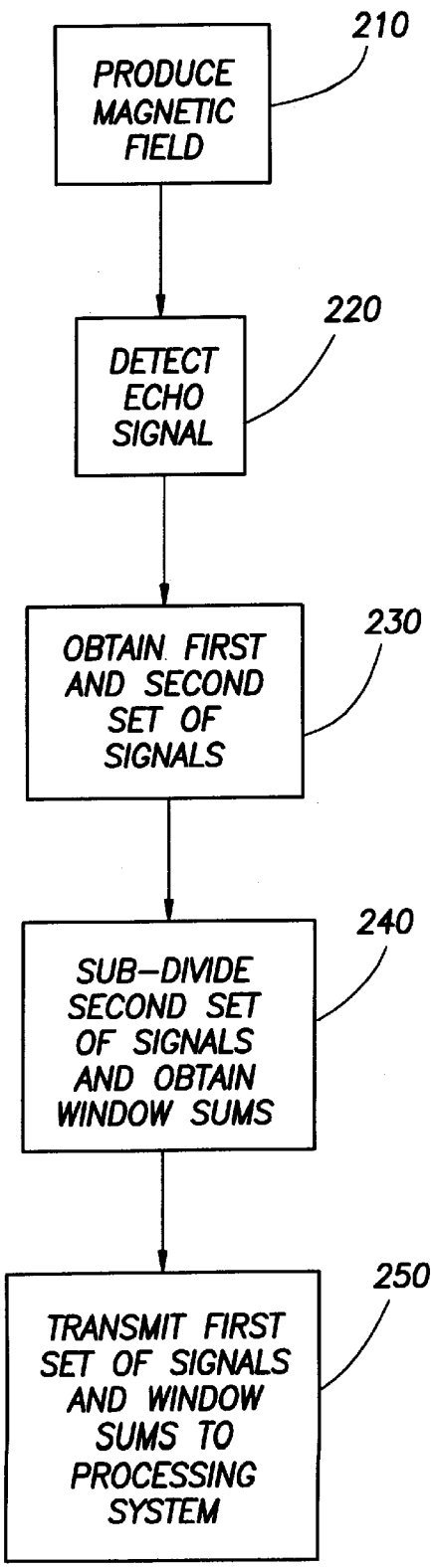
FIG. 4 is a flow chart illustrating steps for determining the total porosity of a formation.

FIG. 4 is a flow chart illustrating the method of the subject invention for determining the total porosity (TCMR) of a formation using an NMR tool. The tool is lowered into the borehole and, at step 210, produces a static magnetic field in the volume of formation and then produces oscillating magnetic fields according to a phase alternated sequence, such as the Carr-Purcell-Meiboom-Gill (CPMG) sequence or a similar pulse sequence, to induce signals in the volume of formation which are measurable by the NMR logging tool according to:

$$W-90°_{\pm x}-(t_{cp}-180°_y-t_{cp}-\text{echo}_j) \tag{3}$$

where j is the index of CPMG echoes gathered, W is the wait time that must precede each CPMG sequence so that the longitudinal magnetization can recover prior to the initial 90° pulse, and $t_{cp}$ is the Carr-Purcell spacing. In a preferred embodiment of the invention, the minimum echo spacing, $2t_{cp}$, is approximately 0.2 ms. The shorter echo spacing improves the number of echoes containing information on clay bound water and, therefore, improves the signal-to-noise ratio on the short $T_2$ signals.

At step 220, the NMR tool detects resulting echo signals which have been induced in the formation around the borehole and determines a value for each signal. At step 230, the echo signals are separated into a first set of signals which consists of the early-time echoes, and a second set of signals which consists of the remaining echoes. The early-time echoes contain contributions from signals having $T_2$ relaxation times less than approximately three milliseconds. The number of early-time echoes is related to the echo spacing. In a preferred embodiment of the invention, with an echo spacing of approximately 0.2 ms, there are approximately six early-time echoes. At step 240, the remaining echoes are sub-divided into a plurality of window bins and a sum for each window bin is determined by summing the echo signals disposed in each window. At step 250, the value for each early-time echo and the plurality of window sums are transmitted uphole from the NMR tool to a processing system disposed at the surface. It is within contemplation of this invention to have the processing system located downhole. The processing system may be located either downhole or uphole. At step 260, an attribute of the formation is determined, such as the volume of clay bound water in the formation, the hydrocarbon saturation of the formation, or the total porosity (TCMR), that is, the sum of free fluid, capillary-bound, and clay-bound porosity. The processing system computes a distribution function, $P(T_2)$, and a total porosity log output responsive to each early-time echo and the plurality of window sums.

In the subject invention, the volume of clay bound water, $\phi_{cbw}$, is determined by integrating the distribution function $P(T_2)$ according to the following equation:

$$\varphi_{cbw} = \int_{T_{min}}^{T_{cbw}} P(T_2)dT_2 \tag{4}$$

where $T_{cbw}$ is a predetermined cut-off relaxation time, for distinguishing clay-bound water. The total porosity, TCMR, is determined by integrating the distribution function $P(T_2)$ according to the following equation:

$$\varphi_{TCMR} = \int_{T_{min}}^{T_{max}} P(T_2)dT_2. \tag{5}$$

Figure 5:
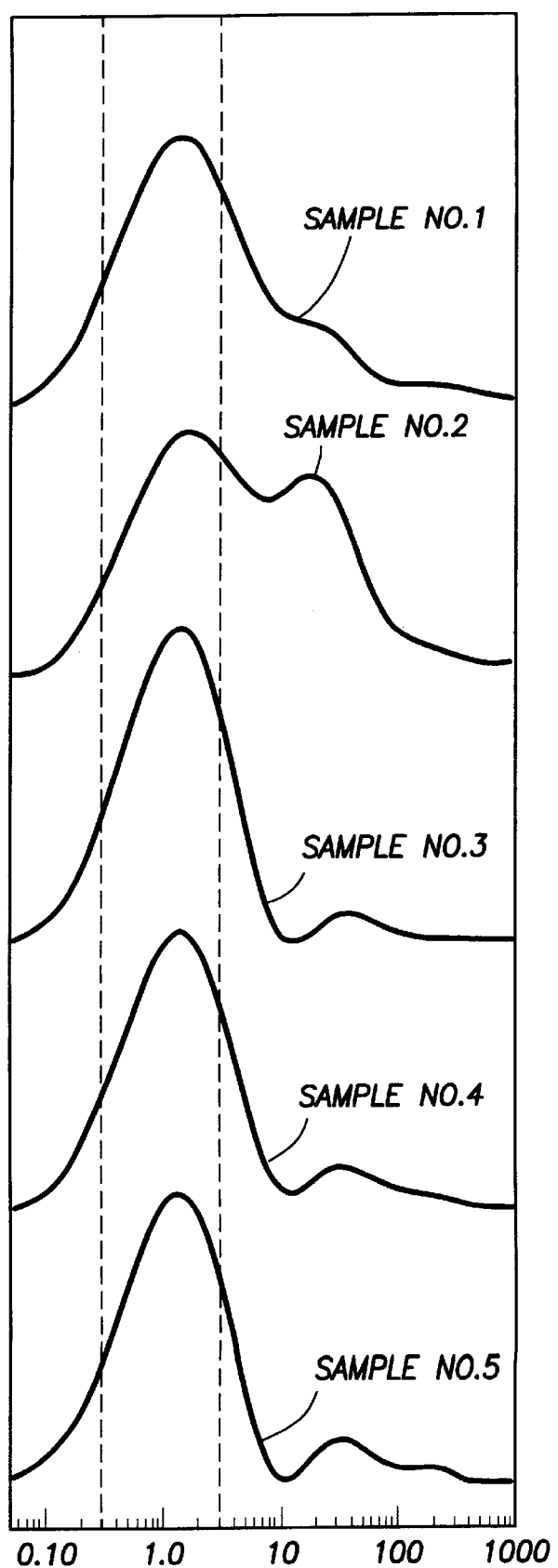
FIG. 5 is a comparison of the $T_2$ distribution using five core samples with a $T_2$ cutoff at 3 msec and 0.3 msec.
Figure 6:
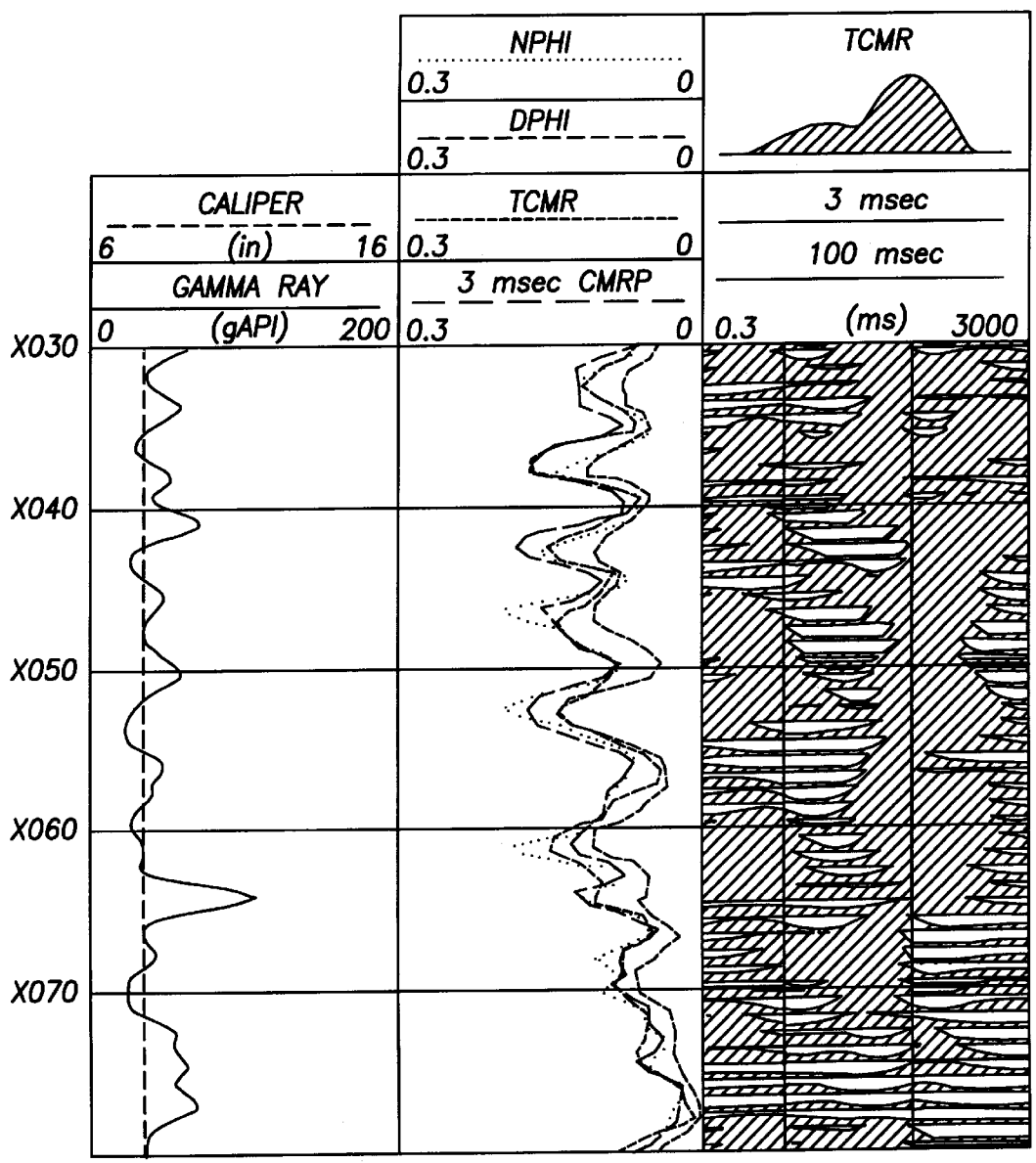
FIG. 6 is a comparison of the effective porosity and total porosity using log outputs.

The TCMR measurement provides additional information on porosity and detects both clay-bound water and microporosity. FIG. 5 shows $T_2$ distributions from core samples extracted from a very shaly sand formation. The porosity exhibited from T=0.3 msec to approximately T=3.0 msec is representative of the difference between TCMR and CMRP. The differences in CMRP and TCMR porosity in this interval are due to microporosity associated with both small pores and clay-bound water. Similarly, FIG. 6 illustrates a comparison of effective porosity (CMRP) and total porosity (TCMR) derived $T_2$ distributions using CMRP and TCMR log outputs from a dolomite formation. The formation has significant amounts of microporosity, as evidenced from the amplitudes on the $T_2$ distributions from T=0.3 msec to approximately T=3.0 msec. Because of the microporosity, the CMRP porosity reads lower than the TCMR porosity over portions of the logged interval. The differences in CMRP and TCMR porosity over the logged interval are due to microporosity associated with both small pores and clay-bound water.

It has been shown that a relation exists between the amount of bound water contained in the pores of a shale bearing formation and the cation exchange capacity of the clay minerals. See H. Hill, O. Shirley, and G. Klein, *Bound Water in Shaly Sands—Its Relation to $Q_v$ and Other Formation Properties*, 20 LOG ANALYST 3–19, (1979). The total porosity measurement provides an effective means for deriving $Q_v$, the cation exchange capacity normalized to the pore volume, from log data using the approach set forth by Hill-Shirley-Klein:

$$Q_v = \frac{\phi_{cbw}}{0.28 * \phi_{TCMR}}. \tag{6}$$

It has been shown that the conductivity of oil-bearing shaly sands can be described by an expression relating the resistivity ratio to water saturation, water resistivity, and the cation exchange capacity per unit pore volume of the formation. See M. Waxman and L. Smits, *Electrical Conductivities in Oil-Bearing Shaly Sands*, 243 Soc'Y OF PETR. ENG. J. 107–122, (1968). The water saturation, $S_w$, is determined using the approach set forth by Waxman-Smits:

$$S_w = \frac{\left(F^* \cdot \frac{R_w}{R_t}\right)^{\frac{1}{n^*}}}{(1 + B \cdot Q_v \cdot R_w / S_w)^{\frac{1}{n^*}}} \tag{7}$$

where $F^*$ is a formation resistivity factor for shaly sand, $R_w$ is the resistivity of equilibrating aqueous salt solution, $R_t$ is the resistivity of a partially water saturated sand, $n^*$ is the saturation exponent for shaly sand, and B is an equivalent conductance of clay exchange cations. The hydrocarbon saturation is determined by the expression $S_{HC}=1-S_w$.

Alternatively, the hydrocarbon saturation is determined according to the dual water model which accounts for the exclusion of salt from a fraction of the pore water. See C. Clavier, G. Coates, and J. Dumanoir, *The Theoretical and Experimental Bases for the "Dual Water" Model for the Interpretation of Shaly Sands*, Soc'Y OF PETR. ENG. TRANS. 6859 (1977). The water saturation, $S_{wt}$, is determined using the dual water model:

$$S_{wt} = \left(\frac{F_0 \cdot C_t}{\beta \cdot Q_v}\right)^{\frac{1}{n-1}} \tag{8}$$

where $F_0$ is a formation resistivity factor for shaly sand as used in the dual water model, $C_t$ is the true conductivity of a hydrocarbon bearing formation, $\beta$ is the equivalent conductivity of sodium counterions, $Q_v$ is the concentration of clay counterions per unit pore volume, and n is the saturation exponent. The hydrocarbon saturation is determined by the expression $S_{HC}=1-S_{wt}$.

Figure 7:
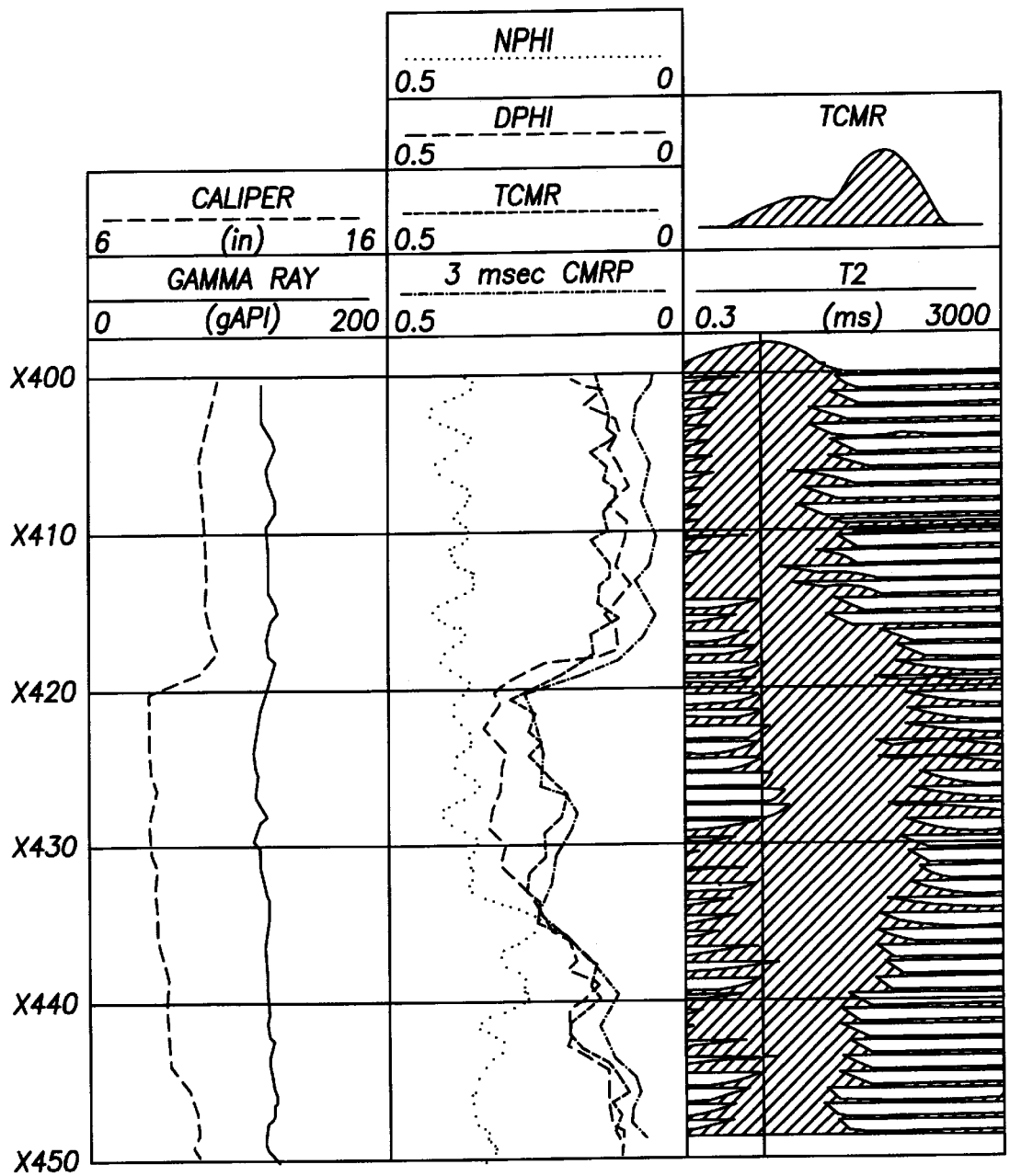
FIG. 7 is a log output from a formation having shale overlying a sand containing gas.

FIG. 7 illustrates a comparison of effective porosity (CMRP), total porosity (TCMR), neutron porosity log (NPHI), and the density porosity log (DPHI) across an interval consisting of shale overlying a gas sand. In the interval from 418 feet to 433 feet, the neutron-density log crossover is suppressed by the shaliness, which opposes the gas effect on the neutron log. The CMRP log does not provide information on $T_2$ values below 3 msec. Therefore, the deficit between the CMRP and density log porosity in the interval from 418 feet to 433 feet can be attributed to clay bound water, microporosity, or reduced hydrogen index caused by gas. Thus, the CMRP-density log porosity difference is an unreliable indicator of gas in shaly sands. On the other hand, the TCMR—density porosity log difference accurately indicates the presence of gas in shaly sands. In the subject invention, the gas saturation, $S_g$, and a gas corrected porosity, $\phi$, are determined according to the following relationship:

$$S_g = \frac{DPHI - TCMR}{DPHI * (1 - HI * P) + \lambda * TCMR}, \tag{9}$$

$$\phi = \frac{DPHI * (1 - HI * P) + \lambda * TCMR}{(1 - HI * P) + \lambda}, \text{ where} \tag{10}$$

$$P = 1 - \exp(-W/T_{1,g}) \text{ and} \tag{11}$$

$$\lambda = \frac{\rho_f - \rho_g}{\rho_{ma} - \rho_f}, \tag{12}$$

where HI is the hydrogen index of gas at reservoir temperature and pressure, P is the polarization factor having a value in the range of 0–1 and characterizes the degree of polarization of the gas, $\lambda$ accounts for gas effect on the density log, W is a wait time of sufficiently length so as to polarize all fluids, excluding gas, $T_{1,g}$ is the spin-lattice relaxation time for gas, $\rho_g$ is the density of gas at reservoir temperature and pressure, $\rho_f$ is the fluid density and $\rho_{ma}$ is the matrix density used to compute DPHI from the measured bulk density.

It has been shown that the permeability of a water saturated sand or an oil bearing sand can be described by relating porosity to the bound fluid volume. In the subject invention, the total porosity measurement provides an effective standalone means for deriving an improved estimate of permeability using the approach set forth by Timur-Coates:

$$k = a(\phi_{TCMR})^4 \left(\frac{\phi_{TCMR} - \phi_{BFV}}{\phi_{BFV}}\right)^2, \tag{13}$$

where $\phi_{TCMR}$ is the total porosity, $\phi_{BFV}$ is the bound fluid (including clay bound water) porosity using a bound fluid cut-off of approximately 33 msec, $\alpha$ is along the order of $10^4$, and k provides an estimated permeability measured in millidarcy. For a gas saturated formation, the gas corrected porosity determined in equation (10) is substituted for the total porosity in equation (13) in order to estimate formation permeability.

Figure 8:
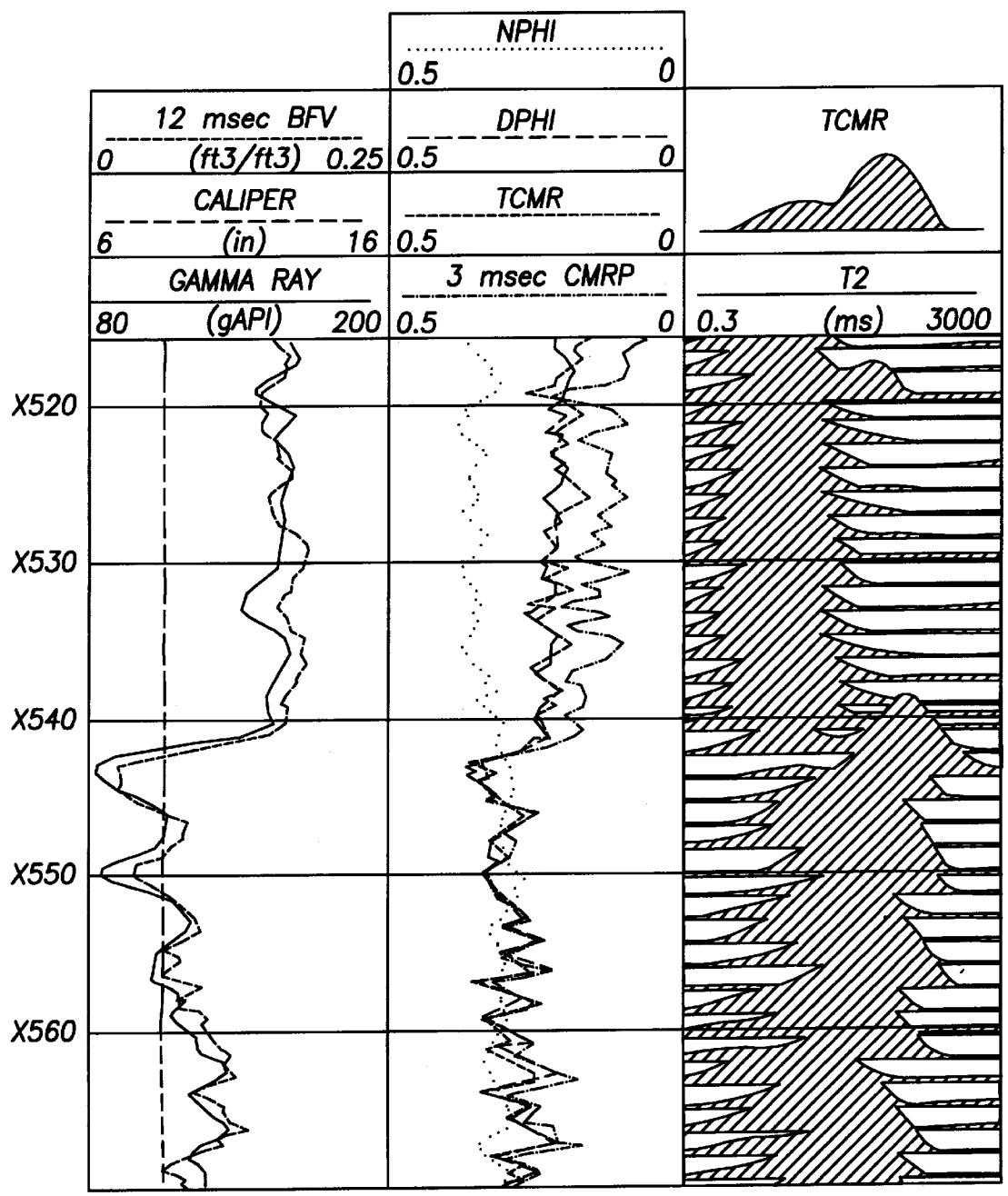
FIG. 8 is a log output from a formation containing a shaly sand.

FIG. 8 indicates a strong correlation between the gamma ray log and the bound fluid porosity with $T_c=12$ msec. A bound fluid volume, $\phi_{bf}$, is determined by integrating the distribution function $P(T_2)$ according to the following equation:

$$\varphi_{bf} = \int_{T_{\min}}^{T_c} P(T_2) dT_2 \tag{14}$$

where $T_c$ is a predetermined cut-off relaxation time of approximately 8 msec to 12 msec, for distinguishing shale. The TCMR measurement provides an accurate shale indicator that is independent of the natural radioactivity of the formation. In some instances, the gamma ray log ineffectively differentiates sand from shale, particularly in cases where the sand contains radioactive minerals such as potassium feldspars.

Figure 9:
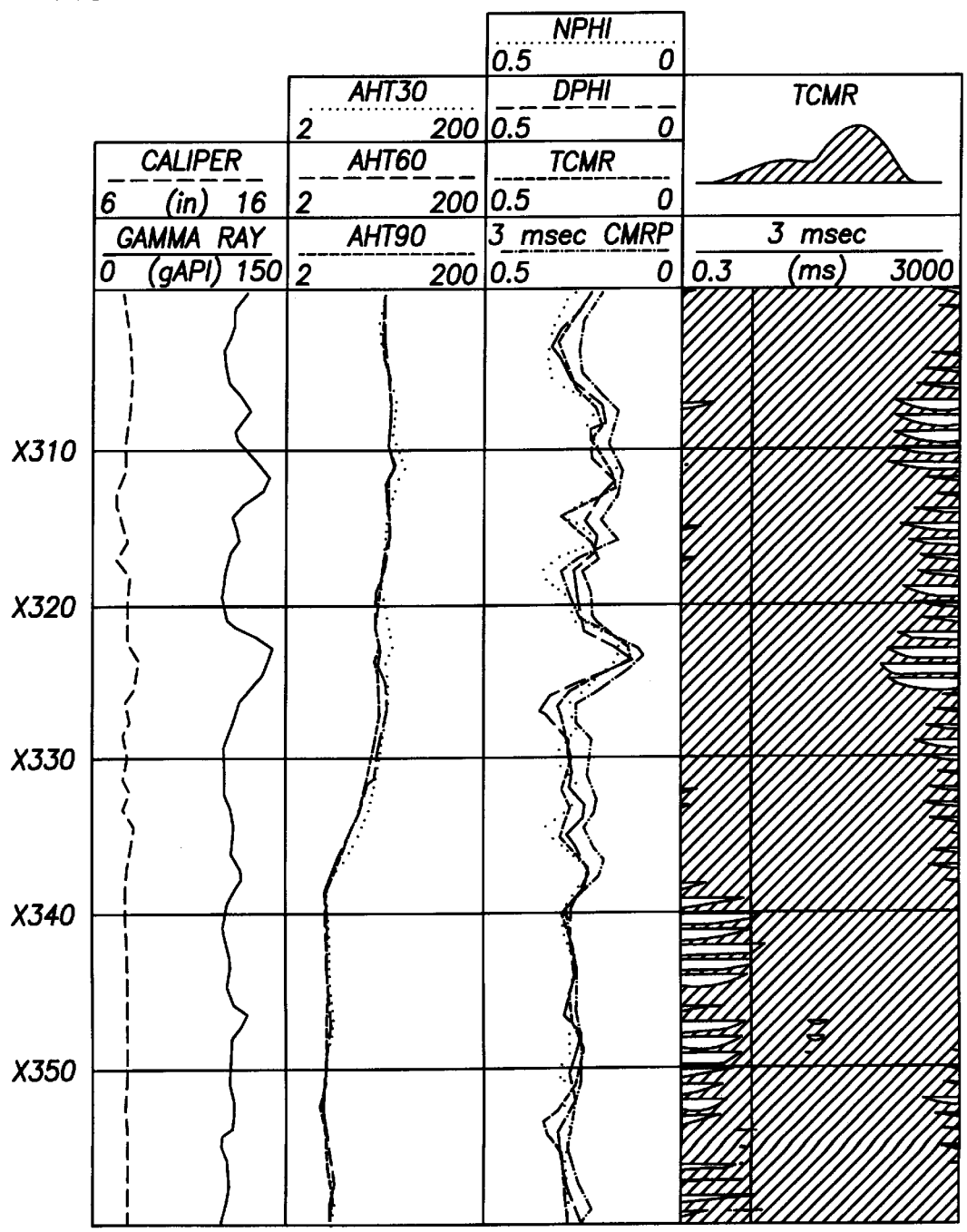
FIG. 9 is a log output from a formation containing viscous hydrocarbons.

Referring to FIG. 9, the responses of the TCMR and CMRP logs in a zone containing viscous hydrocarbons, from 300 feet–338 feet, and in an adjacent lower wet zone provide a clear delineation of the oil zone. The deficit between TCMR and CMRP provides a clear definition of the oil zone. The TCMR measurement provides a means for detecting and quantifying signals from hydrocarbons with viscosities of approximately 10,000 cp.

The foregoing description of the preferred and alternate embodiments of the present invention have been presented for purposes of illustration and description. It is not intended to be exhaustive or limit the invention to the precise form disclosed. While the invention relates to an apparatus and method for measuring total porosity using a nuclear magnetic wireline or logging while drilling tool, the invention is similarly useful for measuring other formation characteristics. Obviously, many modifications and variations will be apparent to those skilled in the art. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What is claimed is:

1. A magnetic resonance method for indicating an attribute of an earth formation traversed by a borehole, comprising the steps of:
   (a) producing oscillating magnetic fields within the borehole in order to induce a plurality of spin echo signals from selected nuclei of the formation;
   (b) measuring the spin echo signals and determining a value for each signal;
   (c) separating the plurality of values into a first set and a second set wherein the first set comprises the early-time echo signals and the second set comprises the remaining echo signals;
   (d) sub-dividing the second set into a plurality of groups;
   (e) generating a window sum value for each group of the second set, thereby producing a plurality of window sums;
   (f) generating a log output and a relaxation time distribution responsive to the plurality of window sums and the value of each signal of the first set;
   (g) determining, from the relaxation time distribution, an indication of the total porosity of the formation;
   (h) generating a log output indicating the density of the formation;
   (i) determining a density porosity of the formation based upon the density log; and,
   (j) determining an attribute of the formation based upon the density porosity and the total porosity.

2. The method of claim 1, wherein the attribute is a gas saturation of the formation.

3. A magnetic resonance apparatus for indicating an attribute of an earth formation traversed by a borehole, comprising:
   (a) a NMR logging tool, the tool further comprising:
      (i) means for producing oscillating magnetic fields in order to induce a plurality of spin echo signals from selected nuclei of the formation; and,
      (ii) means for measuring the spin echo signals and determining a value for each signal;
   (b) means for separating the plurality of values into a first set and a second set wherein the first set comprises the early-time echo signals and the second set comprises the remaining echo signals;
   (c) means for sub-dividing the second set into a plurality of groups;
   (d) means for generating a window sum value for each group of the second set, thereby producing a plurality of window sums;
   (e) means for generating a log output and a relaxation time distribution responsive to the plurality of window sums and the value of each signal of the first set;
   (f) means for determining, from the relaxation time distribution, and indication of the total porosity of the formation;
   (g) means for generating a log output indicating the density of the formation;
   (h) means for determining a density porosity of the formation based upon the density log; and
   (i) means for determining an attribute of the formation based upon the density porosity and the total porosity.

4. The apparatus of claim 3, wherein the attribute is a gas saturation of the formation.

5. A magnetic resonance method for indicating an attribute of an earth formation traversed by a borehole, comprising the steps of:
   determining, from a relaxation time distribution, an indication of the total porosity of the formation;
   generating a log output indicating the density of the formation; determining a density porosity of the formation based upon the density log; and,
   determining a porosity of the formation, corrected for the effect of gas on the log outputs, based upon the density porosity and the total porosity.

6. A magnetic resonance method for indicating an attribute of an earth formation traversed by a borehole, comprising the steps of:
   producing oscillating magnetic fields within the borehole in order to induce a plurality of spin echo signals from selected nuclei of the formation;
   processing the spin echo signals to determine the total porosity of the formation; generating a log output indicating the density of the formation; determining a density porosity of the formation based upon the density log; and, determining a porosity of the formation, corrected for the effect of gas on the log outputs, based upon the density porosity and the total porosity.

7. A magnetic resonance method for indicating an attribute of an earth formation traversed by a borehole, comprising the steps of:
   (a) producing oscillating magnetic fields within the borehole in order to induce a plurality of spin echo signals from selected nuclei of the formation;
   (b) measuring the spin echo signals and determining a value for each signal;
   (c) separating the plurality of values into a first set and a second set wherein the first set comprises the early-time echo signals and the second set comprises the remaining echo signals;
   (d) sub-dividing the second set into a plurality of groups;
   (e) generating a window sum value for each group of the second set, thereby producing a plurality of window sums;

(f) generating a log output and a relaxation time distribution responsive to the plurality of window sums and the value of each signal of the first set;

(g) determining, from the relaxation time distribution, an indication of the total porosity of the formation;

(h) generating a log output indicating the density of the formation;

(i) determining a density porosity of the formation based upon the density log; and, (j) determining a gas corrected porosity of the formation based upon the density porosity and the total porosity.

8. A magnetic resonance apparatus for indicating an attribute of an earth formation traversed by a borehole, comprising:

(a) a NMR logging tool, the tool further comprising:
(i) means for producing oscillating magnetic fields in order to induce a plurality of spin echo signals from selected nuclei of the formation; and,
(ii) means for measuring the spin echo signals and determining a value for each signal;

(b) means for separating the plurality of values into a first set and a second set wherein the first set comprises the early-time echo signals and the second set comprises the remaining echo signals;

(c) means for sub-dividing the second set into a plurality of groups;

(d) means for generating a window sum value for each group of the second set, thereby producing a plurality of window sums;

(e) means for generating a log output and a relaxation time distribution responsive to the plurality of window sums and the value of each signal of the first set;

(f) means for determining, from the relaxation time distribution, and indication of the total porosity of the formation;

(g) means for generating a log output indicating the density of the formation;

(h) means for determining a density porosity of the formation based upon the density log; and (i) means for determining a gas corrected porosity of the formation based upon the density porosity and the total porosity.

* * * * *